US00PP37780P3

(12) United States Plant Patent
Robles et al.

(10) Patent No.: US PP37,780 P3
(45) **Date of Patent: *Oct. 13, 2026**

(54) MUSHROOM VARIETY NAMED 'RO14176'

(50) Latin Name: *Agaricus bisporus Imbach*
Varietal Denomination: RO14176

(71) Applicant: Amycel, LLC, Watsonville, CA (US)

(72) Inventors: Christopher W. Robles, Watsonville, CA (US); Maykoe R. Abaunza, Memphis, TN (US)

(73) Assignee: Amycel, LLC, Watsonville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/305,681

(22) Filed: Aug. 20, 2025

(65) Prior Publication Data

US 2026/0060157 P1 Feb. 26, 2026

Related U.S. Application Data

(60) Provisional application No. 63/733,289, filed on Dec. 12, 2024, provisional application No. 63/685,196, filed on Aug. 20, 2024.

(51) Int. Cl.
*A01H 5/00* (2018.01)
*A01H 15/00* (2006.01)

(52) U.S. Cl.
USPC ..... Plt./394
CPC ..... *A01H 15/00* (2013.01)

(58) Field of Classification Search
USPC ..... Plt./394
See application file for complete search history.

(56) References Cited

U.S. PATENT DOCUMENTS

| | | | |
|---|---|---|---|
| 4,996,390 | A | 2/1991 | Dahlberg |
| 5,304,721 | A | 4/1994 | Kerrigan et al. |
| 7,608,760 | B2 | 10/2009 | Robles et al. |
| 9,017,988 | B1 | 4/2015 | Kerrigan et al. |
| 2010/0212042 | A1 | 8/2010 | Robles et al. |
| 2015/0216127 | A1 | 8/2015 | Kerrigan et al. |
| 2015/0216128 | A1 | 8/2015 | Kerrigan et al. |
| 2020/0084993 | A1 | 3/2020 | Kerrigan et al. |
| 2023/0265379 | A1 | 8/2023 | Amini et al. |
| 2026/0053108 | A1 | 2/2026 | Robles et al. |
| 2026/0060156 | P1 | 2/2026 | Robles et al. |
| 2026/0060158 | P1 | 2/2026 | Robles et al. |

FOREIGN PATENT DOCUMENTS

| | | | |
|---|---|---|---|
| WO | WO-2015127195 | A1 | 8/2015 |
| WO | WO-2016116632 | A1 | 7/2016 |
| WO | WO-2018013603 | A1 | 1/2018 |

OTHER PUBLICATIONS

Castle et al., (1987). "Restriction fragment length polymorphisms in the mushrooms. *Agaricus brunnescens* and *Agaricus bitorquis*," Appl Env Microbiol, 53:816-822.

Castle et al., (1988). "Crosses among Homokaryons from Commercial and Wild-Collected Strains of the Mushroom *Agaricus brunnescens*(=*A. bisporus*)," Appl. Environ. Microbiol., 54:1643-1648.

Hammond et al., (1976). "Carbohydrate metabolism in *Agaricus bisporus* (Lange) Sing: changes in soluble carbohydrates during growth of mycelium and sporophore," Microbiology, 93(2):309-320.

Herbraud et al., (1988). "Protoplast Production and Regeneration from Mycorrhizal Fungi and Their Use for Isolation and Mutants," Can. J, Microbiol, 34: 157-161.

Invitation to pay additional fees received for International Patent Application No. PCT/US2025/042785 mailed on Nov. 21, 2025, 4 pages.

Kerrigan et. al., (1993). "Meiotic Behavior and Linkage Relationships in the Secondarily Homothallic Fungus *Agaricus bisporus*," Genetics, 133:225-236.

Khush et al., (1992). "DNA Amplification Polymorphisms of the cultivated mushroom *Agaricus bisporus*," Appl. Env Micro biol, 59: 2971-2977.

Loftus et al., (1988). "DNA Polymorphisms in Commercial and Wild Strains of the Cultivated Mushroom, *Agaricus bisporus*," Theor. Appl. Genet., 76:712-718.

Mueller et al., (1999). "AFLP genotyping and fingerprinting," Trends Ecol Evol, 14:389-394.

Paran et al., (1993). "Development of reliable PCR-based markers linked to downy mildew resistance genes in lettuce," Theor. Appl. Genet., 85:985-993.

Roerink, (2023). "Mushroom Council's New 10-Year Trends Report Reveals Shifting, Growing Consumer Purchasing Patterns," available online at <https://www.mushroomcouncil.com/press-releases/seizing-the-mushroom-movement/>, 4 pages.

Sonnenberg et al., (1988). "An Efficient Protoplasting/Regeneration System for *Agaricus bisporus* and *Agaricus bitorquis*," Curr. Microbiolo., 17:285-291.

Wakui, (2013) "[Analysis of single nucleotide polymorphisms (SNPs)]," Rinsho Byori., 61(11):1008-1017. English abstract.

(Continued)

*Primary Examiner* — Susan Mccormick Ewoldt
(74) *Attorney, Agent, or Firm* — Morrison & Foerster LLP

(57) ABSTRACT

A new and unique brown variety of the mushroom *Agaricus bisporus* Imbach was produced by crossing the progeny of brown mushrooms and off-white hybrid mushrooms to bridging cross strains. The resultant hybrid, named 'RO14176', exhibits distinct and stable characteristics. Hybrid 'RO14176' exhibits a light cap color, thicker cap flesh, rounder cap, faster mushroom development, and higher yield, especially when compared to available brown mushroom varieties.

5 Drawing Sheets

(56) References Cited

OTHER PUBLICATIONS

Unpublished U.S. Appl. No. 19/305,679, filed Aug. 20, 2025, titled "Mushroom Variety 'RO10425'," (not submitted herewith pursuant to the waiver of 37 C.F.R. § 1.98(a)(2)(iii)).
Unpublished U.S. Appl. No. 19/305,681, filed Aug. 20, 2025, titled "Mushroom Variety 'RO14176'," (not submitted herewith pursuant to the waiver of 37 C.F.R. § 1.98(a)(2)(iii)).
Unpublished U.S. Appl. No. 19/305,683, filed Aug. 20, 2025, titled "Mushroom Variety 'RO12756'," (not submitted herewith pursuant to the waiver of 37 C.F.R. § 1.98(a)(2)(iii)).
International Search Report and Written Opinion received for International Patent Application No. PCT/US2025/042785 mailed on Jan. 21, 2026, 17 pages.
Sonnenberg et al., (2017). "Developments in breeding of *Agaricus bisporus* var. *bisporus*: progress made and technical and legal hurdles to take," Appl Microbiol Biotechnol, 101:1819-1829.

MUSHROOM VARIETY NAMED 'RO14176'

Latin name: Genus and species: The mushroom cultivars of this disclosure are identified as *Agaricus bisporus* Imbach.

Varietal denomination: Variety denomination: The variety denomination is 'RO14176'.

BACKGROUND OF THE INVENTION

The cultivated white button variety of *Agaricus bisporus*, known as *A. bisporus* (Lange) Imbach (syn. *A. brunnescens* Peck), is the predominant mushroom species in cultivation in the world today. After many years in which commercial mushroom sales in the United States were restricted primarily to white-capped *A. bisporus* mushrooms, there has been a recent trend toward increased sales of brown-capped *A. bisporus* mushrooms of various types and other so-called exotic strains (species other than *A. bisporus*). Improved agronomic characteristics can be introduced into the hybrid strains that can influence producer profitability. For instance, strains may have different ancestry, which will be reflected directly by the genotype and indirectly, in some cases, by the phenotypical characteristics. Generally speaking, strains may be differentiated on the basis of traits associated with the hybrid strains, such as, but not limited to, cap shape, surface texture, flesh thickness, color, shelf life, basidial spore number, sporelessness, resistance to infection by, symptoms of, or transmission of bacterial, viral or fungal diseases, amongst many other traits, to give some examples. Many of these traits directly contribute to factors that influence productivity, revenue capture, reduced costs, crop performance, and consumer and market demand.

In the endeavor to produce new mushroom varieties possessing desirable and improved characteristics, a preferred method is the crossing of homokaryons, 'homokaryons' being a multinucleate haploid fungal culture possessing a single line (somatic lineage) that is capable of undergoing plasmogamy with one or more other homokaryons. Each genetically different homokaryon is representative of a parent line in a resultant heterokaryon. The degree of success of each strain and the profitability of producers can be improved by the appropriate selection of the parental lines. Additionally, improved visual appeal and improved shelf-life, amongst many other characteristics, can also contribute to increased sales for mushroom growers in the world today. Thus, there are many characteristics by which a novel strain might be judged as superior in a particular production facility or a sales market, regionally or globally.

It is also well understood that an industry relying extensively only on a single genetic lineage is at increased risk of unpredictable, catastrophic crop failure on a worldwide scale due to the spread of diseases. To alleviate this type of problem, development and cultivation of new hybrid strains with independent lineages will help to act as a disease break. Further, it is highly desirable to simultaneously provide both genetic diversification and commercially acceptable improved crop characteristics. Thus, the need continues to exist for new brown hybrid strains of *Agaricus bisporus* with improved and preferred characteristics.

BRIEF SUMMARY OF THE INVENTION

It is an object of the disclosure to provide a brown variety of *Agaricus bisporus* mushroom with improved commercial characteristics relative to existing brown commercial mushrooms. Strains of the new brown variety, as well as qualities of this new variety, are described herein.

The following traits have been repeatedly observed and are determined to be the unique characteristics of the novel brown *Agaricus bisporus* mushroom strains. Specifically, it is an object of the disclosure to provide mushrooms that have one or more (most preferably all) of these following characteristics (relative to brown *Agaricus bisporus* now being marketed).

These characteristics in combination distinguish 'RO14176' as a new and distinct brown variety:

1. Faster or as fast timing to reach pinset, first break, and second break as marketed brown varieties.
2. Higher or as high yield in first break, second break, third break. and overall yield as marketed brown varieties.
3. Medium-dark brown cap color.
4. Higher tray coverage than marketed brown varieties.
5. Cap apex flesh thicker than marketed brown varieties.
6. Cap edge flesh thicker than marketed brown varieties.
7. Round cap shape.
8. Cap height taller or as tall as marketed brown varieties.
9. Incompatibility with other available brown strains.
10. Descent from a commercial off-white hybrid *Agaricus bisporus* mushroom variety (Amycel® XXX).
11. Descent from a bridging cross-strain.

These and other objects of the disclosure have been accomplished by providing a hybrid *Agaricus bisporus* mushroom strain obtained by crossing a mushroom of wild strain AA-0096 or a progeny thereof with a second *Agaricus bisporus* strain comprising a commercial off-white hybrid strain (Amycel® XXX), wherein the mushroom of the disclosure (1) has (a) at least one genetic characteristic of wild strain AA-0096 not present in the second *Agaricus bisporus* strain, (b) at least one genetic characteristic of the second *Agaricus bisporus* strain not present in wild strain AA-0096, and (c) at least one genetic characteristic of the bridging cross strain and (2) has at least one physical characteristic selected from the group consisting of speed to reach pinset, first break, and second break; cap color; cap apex flesh thickness; cap edge flesh thickness; cap texture; tray coverage; speed of harvestable yield in each break; amount of yield in each break; and overall yield that is statistically different from the corresponding physical characteristic of comparison strains 'BR06' (U.S. Pat. No. 7,608,760 B1) or 'B14528' (U.S. Pat. No. 9,017,988 B1).

Another feature of the present disclosure includes a new brown hybrid mushroom having improved agronomic traits leading favorably to increased consumer and market demand, productivity, crop performance, and revenue. Of particular interest and novel advantage are the following traits exhibited by 'RO14176':

1. Higher overall yield, driven by increased yield at later breaks, which enable growers to achieve higher yield per unit area compared to other commercial brown mushrooms.
2. Faster developmental timing, which enables growers to increase their efficiency by allowing them to pick off mushrooms before the end of the growing cycle. Faster strains might also allow for more crops per year. Traits herein related to developmental timing include Days to Pinset, Days to 1st Break, Days to 2nd Break, and Percent Harvested Speed.
3. Thick-fleshed morphology, which reflects higher quality than other commercial brown mushrooms. This morphology remains more consistent at later breaks for 'RO14176' when compared to other commercial varieties, and this increases visual appeal of sliced product. Pre-sliced button mushrooms have been growing in popularity over the last 10+ years; a 10-year report on mushroom sales trends demonstrated that sliced product has eclipsed whole product fresh mushroom sales, encompassing over 50% of fresh brown mushrooms sold in 2023 in the United States (Roerink, A. (2023, October). Ten-year Trends in Fresh Mushroom Sales. Mushroom Council. Available on the worldwideweb at mushroomcouncil[dot]org/wp-content/uploads/2023/10/Ten-Year-Fresh-Mushroom-Trends[dot]pdf).

DETAILED BOTANICAL DESCRIPTION

Figure 1:
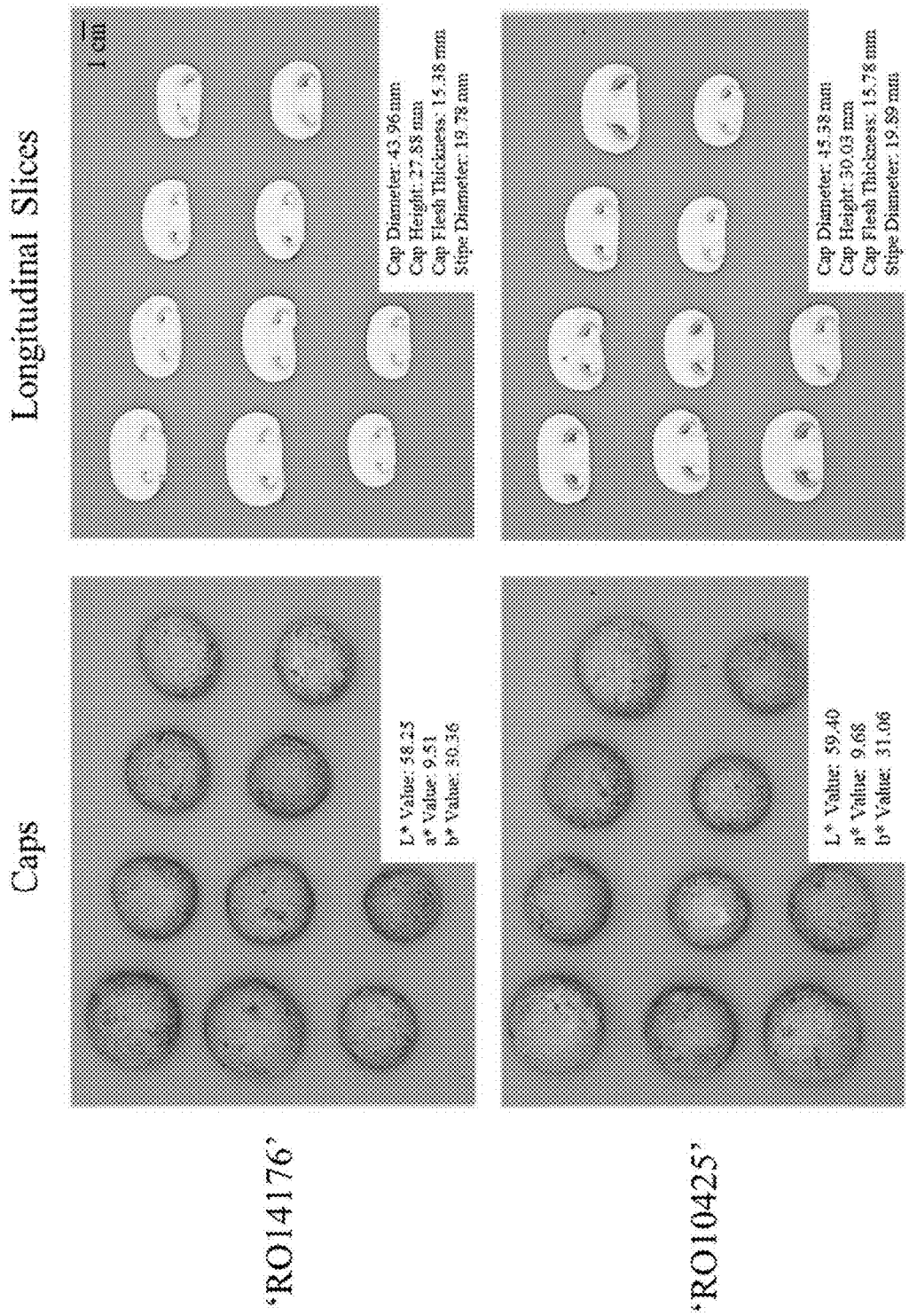
FIG. 1 shows comparisons between mushrooms of variety 'RO14176' (top row) and variety 'RO10425' (bottom row). The top left panel shows caps of 10 representative mushrooms from variety 'RO14176' and their average L*, a*, and b* values. The top right panel shows a longitudinal slice of each mushroom cap in the top left panel with the 10 mushrooms' average cap diameter, cap height, cap flesh thickness, and stipe diameters reported in millimeters. The bottom left panel shows caps of 10 representative mushrooms from variety 'RO10425' and their average L*, a*, and b* values. The bottom right panel shows a longitudinal slice of each mushroom cap in the bottom left panel with the 10 mushrooms' average cap diameter, cap height, cap flesh thickness, and stipe diameters reported in millimeters. Mushrooms pictured were grown in the same room, under the same environmental conditions, and were harvested from the same trial in April 2025. All photos have the same scale. Scale bar=1 cm.

In mushroom breeding, mycelial (=vegetative) cultures of two compatible progenitors (typically these are haploid homokaryotic strains called homokaryons) must come into physical contact so that one or more fusion zones can occur between the progenitors. Within those fusion zones nuclei from the two progenitors become associated. In *Agaricus bisporus*, a novel, hybrid mycelium ultimately containing two compatible haploid nuclear types (one from each of the two progenitors) plus one mitochondrial type (from either one of the progenitors) emerges. This novel hybrid mycelium can be isolated and propagated to provide the new hybrid culture, which can be further subdivided and propagated for commercial or other purposes.

It should be recognized that the mushrooms of the present disclosure are hybrids (equivalent to crosses), as they are formed by the hybridization of at least two independently derived strains, since they were formed by hybridizing the wild strain AA-0096 with a second, commercialized strain of *A. bisporus* (with the second strain, in some embodiments, being itself a cross between at least two other identified strains of *A. bisporus*, i.e., Amycel® XXX). The term 'hybrid mushroom' may be used herein to represent the product of a cross between a wild *A. bisporus* strain and a commercial strain, often including a cross between a brown mushroom strain and an off-white hybrid variety (Amycel® XXX). Differences in terminology (and in the specific techniques used alongside the terminology) are merely indicative of the variety of terminology and techniques used in the mushroom production field.

After parental homokaryotic spores germinated into mycelia, single spore isolates (SSIs) were selected, preferentially those exhibiting slow mycelial growth. The slowly growing mycelia of SSIs usually contain one nuclear type, are thus homokaryotic, and are suitable for crossing, and thus for breeding. Slow growers are denoted as "sg". Some homokaryons were obtained through protoplasting; this technique involves treating the vegetative mycelia of the heterokaryons to damage the fungal cell wall, then selecting colonies of protoclones that are each derived from a single, regenerated protoplast. All crosses were initially cultivated on a small scale, and spores were collected for the parents of the crosses to produce the hybrids described herein.

One useful feature in the breeding programs for these novel mushroom varieties is the use of a bridging cross strain, which is a hybrid variety produced from crossing a commercial brown variety with a commercial white variety. The particular bridging cross strain of note in these breeding programs is known as the 4×29 strain. Strain 4×29 has been previously deposited under the provisions of the Budapest Treaty with the American Type Culture Collection, Rockville, Md., USA, ATCC accession No. PTA-6877 (deposited on Jul. 20, 2005). Strain 4×29 is the product of crossing a commercial brown strain with a commercial white strain. The '29' of this strain is a unique homokaryon collected from an off-white hybrid strain.

The varieties, mushrooms, strains, and cultures disclosed herein are understood to comprise parts of mushrooms, such as the fruiting body, cap, stipe, basidium, spore, mycelium, mixed or unmixed spawn, inoculated substrate, or product produced from the mushroom. In some embodiments, the mushroom part from the hybrid mushroom produced by any method disclosed herein is a spore. In some embodiments, the mushroom part produced from a mushroom strain disclosed herein is a spore. In some embodiments, 'RO14176' is a mushroom part produced from the hybrid mushroom of 'RO10425' (U.S. application Ser. No. 19/305,679). In some embodiments, the mushroom part produced from the hybrid mushroom of 'RO10425' is 'RO14176'. FIG. 1 compares caps and longitudinal mushroom slices of 'RO14176' and 'RO10425'.

Trait Determinations

Figure 2:
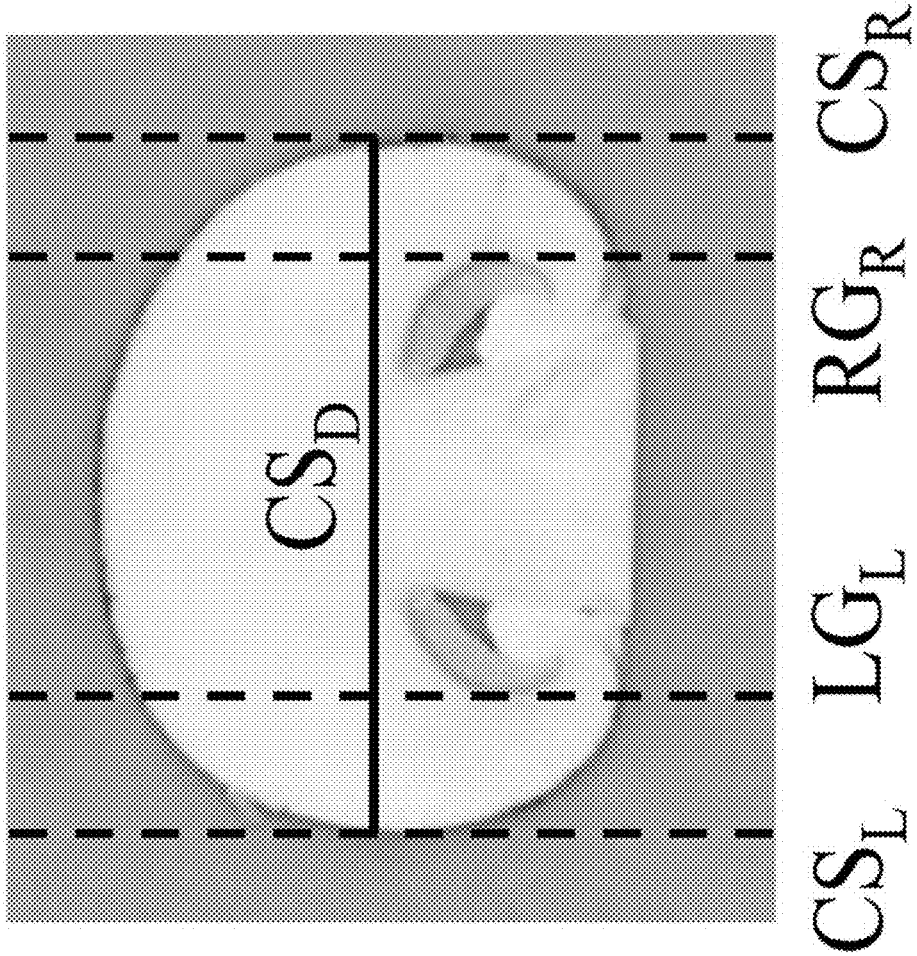
FIG. 2 shows a longitudinal slice of a mushroom of variety 'RO14176' with markings added to illustrate the calculation of Cap Edge Flesh Thickness, where Cap Edge Flesh Thickness is calculated by $((LG_L-CS_L)+(CS_R-RG_R))/CS_D$. $LG_L$=left-most x-coordinate of the left gill, $CS_L$=left-most x-coordinate of the cross-section, $CS_R$=right-most x-coordinate of the cross-section, $RG_R$=right-most x-coordinate of the right gill, and $CS_D$=diameter of the cross-section.
Figure 3:
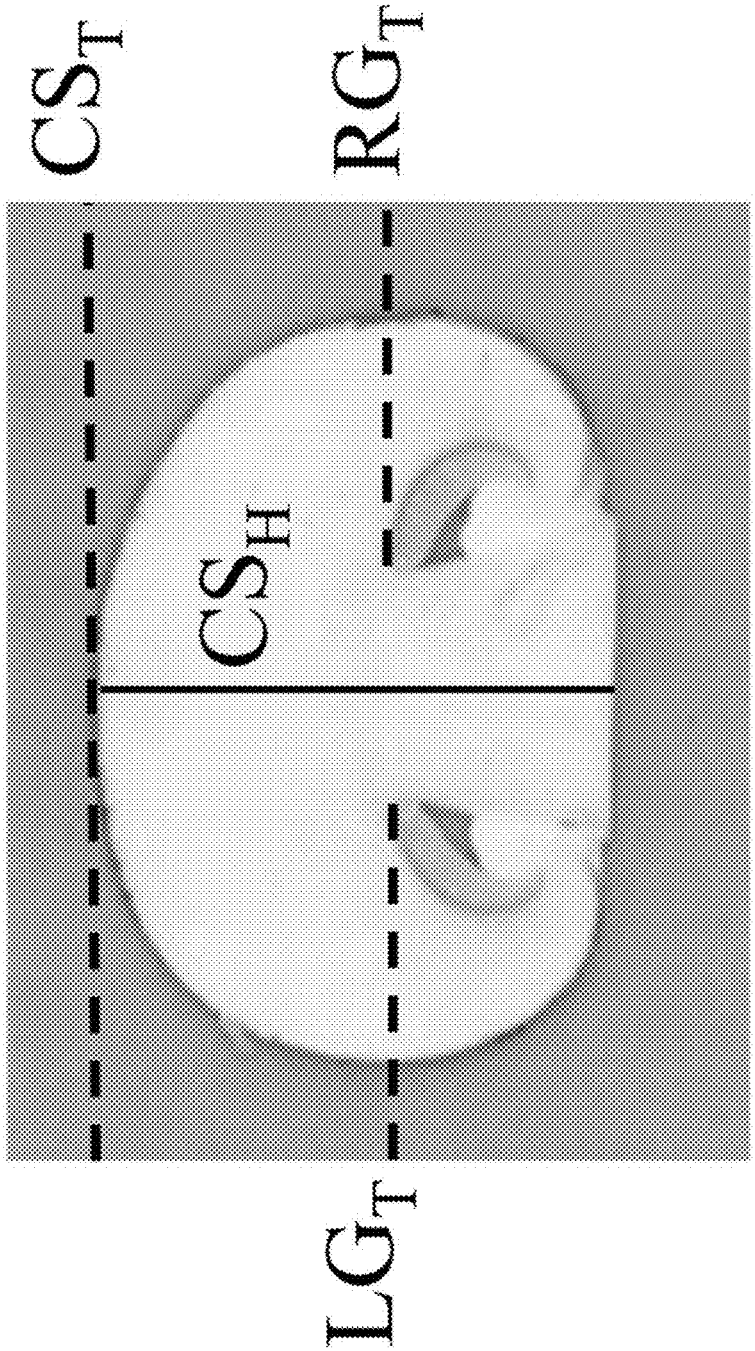
FIG. 3 shows a longitudinal slice of a mushroom of variety 'RO14176' with markings added to illustrate the calculation of Cap Apex Flesh Thickness, where Cap Apex Flesh Thickness is calculated by $(CS_T-((LG_T+RG_T)/2))/CS_H$. $CS_T$=the top-most y-coordinate of the cross-section, $LG_T$=the top-most y-coordinate of the left gill, $RG_T$=the top-most y-coordinate of the right gill, and $CS_H$=the height of the cross-section.

In the descriptions and tables that follow, numerous traits are calculated/measured as follows in Table 1. Visual depictions of the measurements used for calculating Cap Apex Flesh Thickness are shown in FIG. 3. Visual depictions of the measurements used for calculating Cap Edge Flesh Thickness are shown in FIG. 2.

Mushrooms were harvested at Stage 3 as described by Hammond & Nichols (Hammond, J. B. W., & Nichols, R. (1976). Carbohydrate metabolism in *Agaricus bisporus* (Lange) Sing.: changes in soluble carbohydrates during growth of mycelium and sporophore. Microbiology, 93(2), 309-320), when cap diameters were approx. 3-5 cm with the veil still intact. To reduce confounding effects introduced by different trials, developmental timing and yield traits were compared only from trials where all strains being compared were present together.

Images of mushroom caps and longitudinal cross-sections were captured using a Canon Rebel SL1 camera (Canon, Inc., Toyko, Japan) in a custom-built photo box with standardized lighting conditions. The camera was calibrated for color consistency using a ColorChecker gray balance card (Calibrite LLC, Wilmington, DE). L*, a* and b* values were captured across the surface of each mushroom cap and cross-section using ImageJ (Schneider, C. A., Rasband, W. S., & Eliceiri, K. W. (2012). NIH Image to ImageJ: 25 years of image analysis. Nature Methods, 9(7), 671-675). Images captured in 2024 and 2025 were used for analysis. Extreme outliers were excluded from the data, defined as those falling 3 times the interquartile range (IQR) above the 75th percentile for that trait or more than 3 times the IQR below the 25th percentile for that trait.

All statistical analyses were carried out in the R programming language (R Core Team, (2013). R: A language and environment for statistical computing. R Foundation for Statistical Computing, Vienna, Austria. Available on the worldwide web at R-project[dot]org/). Levene's test was performed using the 'car' package (Fox, J., & Weisberg, S. (2018). An R companion to applied regression. SAGE Publications), Shapiro-Wilk tests and Tukey HSD were performed using the 'stats' package (R Core Team (2013)), and standard ANOVAs, Kruskal-Wallis tests and Dunn's tests were performed using the 'rstatix' package (Kassambara, A (2023). rstatix: Pipe-Friendly Framework for Basic Statistical Tests. R package version 0.7.2, rpkgs[dot]datanovia[dot]com/rstatix/).

TABLE 1

Trait descriptions corresponding to the information presented in the "Objective description of the variety 'RO14176'" and the "Comparisons to Commercial Mushroom Varieties" sections.

| Trait | Tool | Measurement Scale | Timing |
|---|---|---|---|
| Cap Color Dark-ness | visually assessed | 0 to 5 (from white to dark brown), tray-level measurement | 1st break**, 2nd break** |
| Cap Color a* Value (Green-Red) | image analysis | −128 to +127 (from pure green to pure red), individual mushroom-level measurement | 1st break**, 2nd break** |
| Cap Color b* Value (Blue-Yellow) | image analysis | −128 to +127 (from pure blue to pure yellow), individual mushroom-level measurement | 1st break**, 2nd break** |

TABLE 1-continued

Trait descriptions corresponding to the information presented in the "Objective description of the variety 'RO14176'" and the "Comparisons to Commercial Mushroom Varieties" sections.

| Trait | Tool | Measurement Scale | Timing |
|---|---|---|---|
| Cap Color L* Value (Dark-Light) | image analysis | 0 to 100 (from pure black to pure white), individual mushroom-level measurement | 1st break**, 2nd break** |
| Cap Dia-meter | image analysis | millimeters (mm), individual mushroom-level measurement | 1st break**, 2nd break** |
| Cap Firm-ness | manual squeeze test | 1 to 5 (from very soft to very firm), tray-level measurement | 1st break**, 2nd break** |
| Cap Apex Flesh Thick-ness | calculated ratio and image analysis | distance from top of gills to top of cap of mushroom, relative to cap height, individual mushroom-level measurement | 1st break**, 2nd break** |
| Cap Edge Flesh Thick-ness | calculated ratio and image analysis | sum of distances from outer edge of each gill to outer edges of cap of mushroom, relative to cap diameter, individual mushroom-level measurement | 1st break**, 2nd break** |
| Cap Flesh Thick-ness | hand-measure-ment | millimeters (mm), distance from top of gill-stipe connection (at center of stipe) to top of cap, individual mushroom-level measurement | 1st break**, 2nd break** |
| Cap Height | image analysis | millimeters (mm), distance from base of cap to top of cap, individual mushroom-level measurement | 1st break**, 2nd break** |
| Cap Round-ness (Cal-culated) | image analysis | Unitless ratio (0-1), calculated as $4 * CS_A / (\pi * CS_D^2)$, where $CS_A$ = area of the cross-section, and $CS_D$ = diameter of the cross-section; assessed with image analysis, | 1st break**, 2nd break** |

TABLE 1-continued

Trait descriptions corresponding to the information presented in the "Objective description of the variety 'RO14176'" and the "Comparisons to Commercial Mushroom Varieties" sections.

| Trait | Tool | Measurement Scale | Timing |
|---|---|---|---|
| | | individual mushroom-level measurement | |
| Cap Roundness (Visual) | visually assessed | 1 to 5 (from very flat to spherical), tray-level measurement | 1st break**, 2nd break** |
| Compatibility | calculated ratio | pounds per square foot (lb/ft$^2$) and kilograms per square meter (kg/m$^2$), weight of 1st break mushrooms yielded relative to area of tray, tray-level measurement | 1st break** |
| Compost Colonization | visually assessed | 0 to 5 (from no colonization to robust colonization), tray-level measurement | before 1st break (10 days after spawning) |
| Days to 1st Break | visually assessed | number of days elapsed after casing at which at least half of tray is of harvestable maturity for 1st break, tray-level measurement | 1st break ** |
| Days to 2nd Break | visually assessed | number of days elapsed after casing at which at least half of tray is of harvestable maturity for 2nd break, tray-level measurement | 2nd break** |
| Days to Pinset | visually assessed | number of days elapsed after casing at which pins first reach 5 mm, tray-level measurement | before 1st break |
| Percent Harvested Speed | calculated ratio | % of yield harvested by a designated date within break, yield at date within break/total yield for break, trial-level measurement | 17 days after casing (1st break), 24 days after casing (2nd break), 32 days after casing (3rd break) |
| Relative Cap Flesh Thickness | calculated ratio | Cap Flesh Thickness Value/Cap Diameter Value, individual mushroom-level measurement | 1st break**, 2nd break** |
| Relative Cap Height | calculated ratio | Cap Height Value/Cap Diameter Value, individual mushroom-level measurement | 1st break**, 2nd break** |
| Relative Stipe Diameter | calculated ratio | Stipe Diameter Value/ Cap Diameter Value, individual mushroom-level measurement | 1st break**, 2nd break** |
| Stipe Diameter | hand-measurement | millimeters (mm), stipe diameter at base of cap, individual mushroom-level measurement | 1st break**, 2nd break** |
| Tray Coverage | visually assessed | 0 to 5 (from no coverage to full coverage), tray-level measurement | 1st break**, 2nd break** |
| Yield (Each Break) | weighing | kg/m$^2$, tray-level measurement; or lb/ft$^2$, tray-level measurement | Assessed cumulatively throughout 1st, 2nd, and 3rd breaks |
| Yield (Total) | weighing | kg/m$^2$, tray-level measurement; or lb/ft$^2$, tray-level measurement | Assessed cumulatively across 1st, 2nd, and 3rd breaks |

**at date when at least half of tray is of harvestable maturity in break

OBJECTIVE DESCRIPTION OF THE VARIETY 'RO14176'

The following detailed description sets forth the breeding procedures and the characteristics of new cultivar designated 'RO14176'. The strain is maintained and asexually propagated as vegetative mycelium. Spawn (inoculum for the substrate compost) is prepared from the vegetative mycelium. Specifically, the strain has been asexually propagated and maintained by vegetative mycelium in Royal Oaks, California, USA. The variety has shown uniformity and stability for the traits, within the limits of expected environmental influence for the traits.

All homokaryons utilized are strains of *Agaricus bisporus*.

'RO14176' was produced as a heterokaryon SSI derived from strain 'RO10425'.

The nearest color on The Colour Chart of The Royal Horticultural Society of London (R.H.S.) (2015 edition) color chart was identified by Eucliean distance in the International Commission on Illumination (CIELAB) color space, carried out using the farver package in R:

'RO14176' Cap color: RHS 199D (dark greyish yellow)

'RO14176' Stipe color: RHS 159B (pale orange yellow)

'RO14176' Gill color: RHS N170D (moderate yellowish pink)

'RO14176' sets pins and produces harvestable mushrooms at first break and second break as fast or faster than available brown commercial strains. 'RO14176' additionally exhibits higher yield at third break, and higher overall yield, than available brown commercial strains. 'RO14176' also exhibits rounder cap shape, thicker cap apex flesh, thicker cap edge flesh, and a new cap color compared to available brown commercial strains. 'RO14176' additionally exhibits percent harvested speed faster or as fast as other available brown commercial strains.

Other characteristics of 'RO14176' distinguishable from other varieties are described below (compared to commercial line 'BR06' and commercial line 'B14528').

Figure 4:
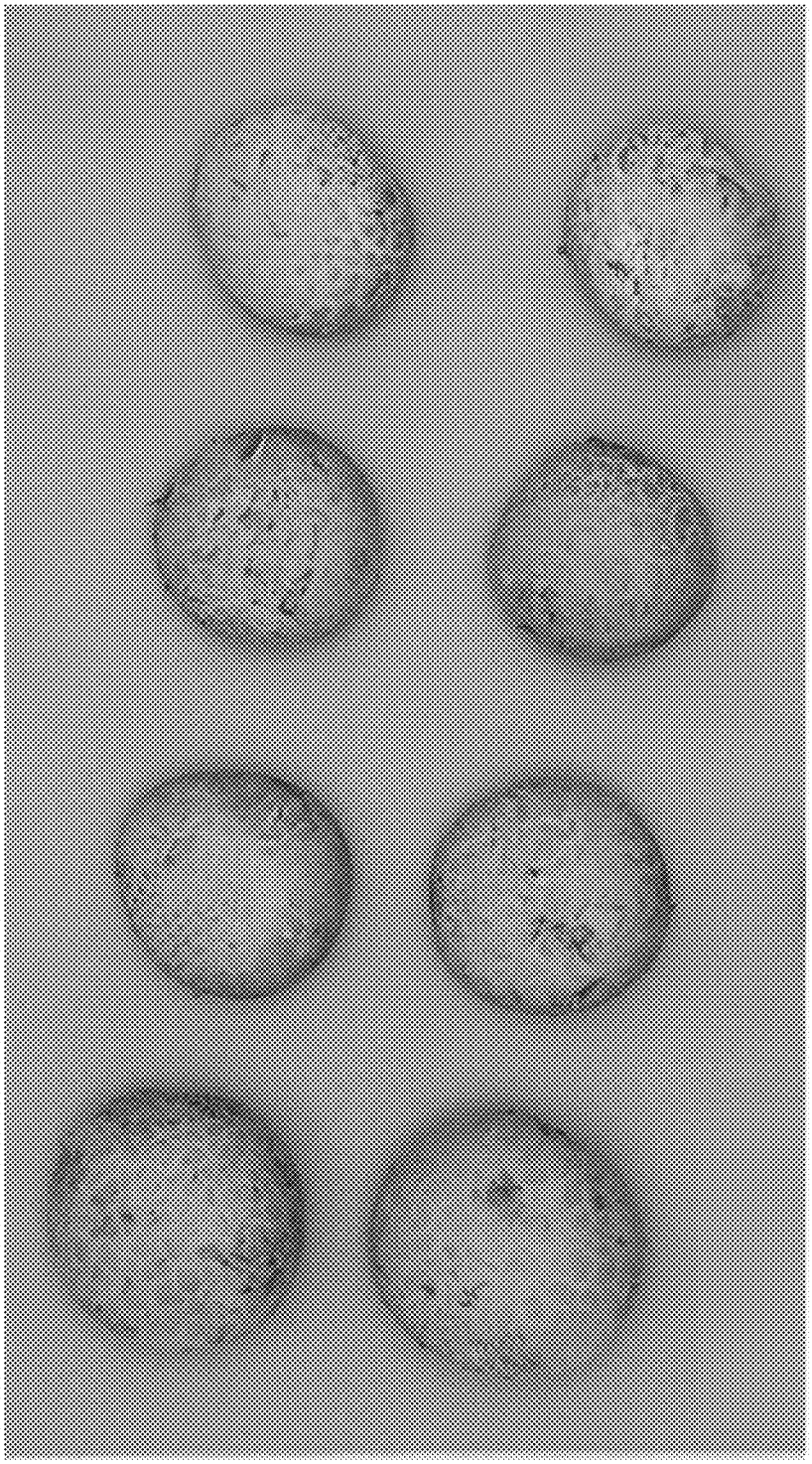
FIG. 4 shows multiple mushroom caps of variety 'RO14176' from a top-down view.
Figure 5:
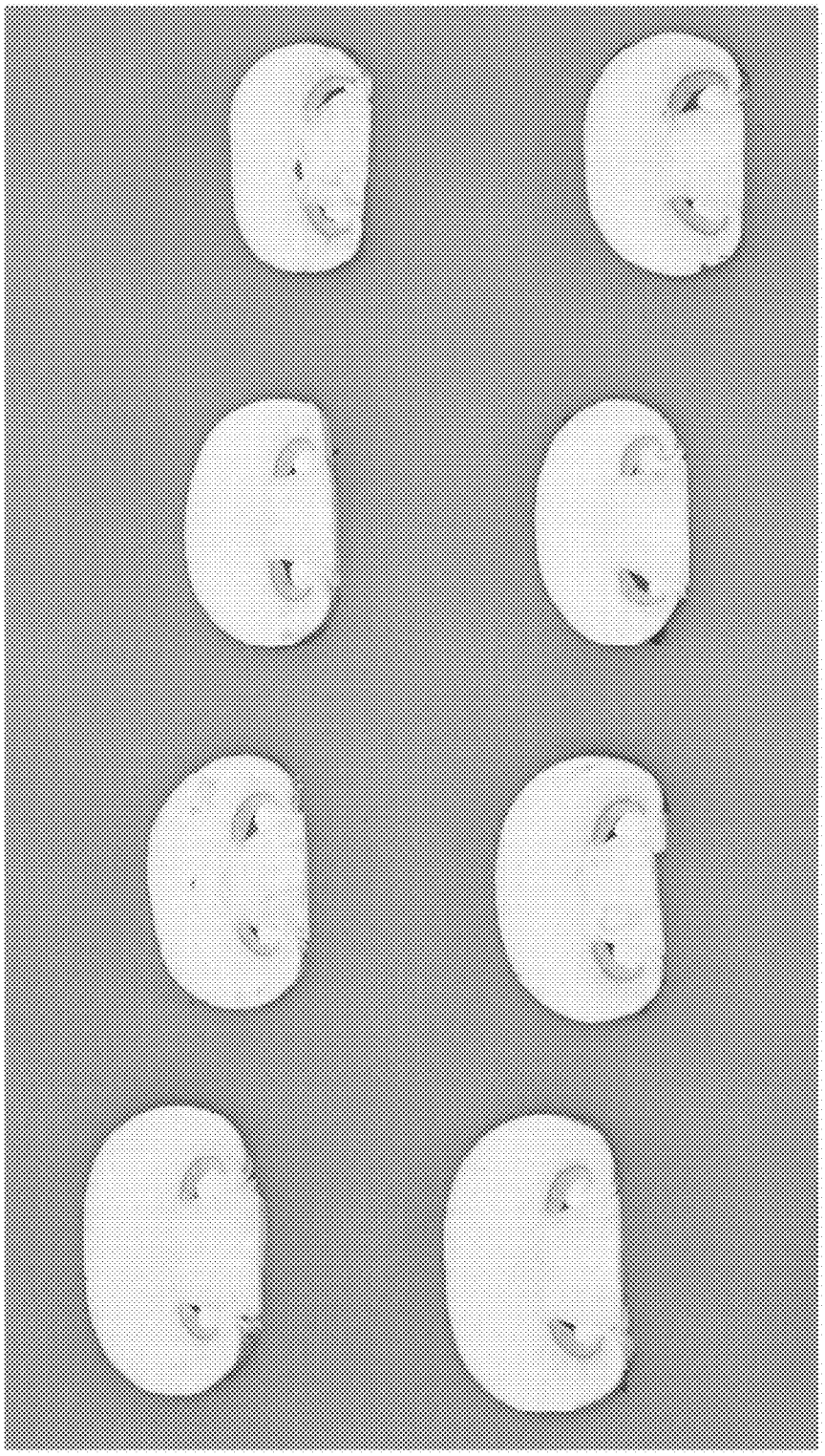
FIG. 5 shows multiple longitudinal slices of mushrooms of variety 'RO14176'.

FIG. 4 and FIG. 5 show mushroom caps and longitudinal slices, respectively, of strain 'RO14176'.

COMPARISONS TO COMMERCIAL MUSHROOM VARIETIES

Initial Trials

Tray-Level Comparisons

In further evidence of the distinctness and superiority of mushroom strain 'RO14176', provided below are the results of trials conducted across multiple strains' yielded trays of mushrooms. These trials compare timing for trays to reach pinset and harvestable maturity, tray coverage, cap color darkness, cap firmness, cap roundness (visual), and yield at each break. Characteristics were measured from 46 trays of strain 'RO14176' mushrooms for yield traits and from 26 trays of strain 'RO14176' mushrooms for other traits. Corresponding measurements were taken from 38 trays of strain 'BR06' mushrooms for yield traits and 19 trays of strain 'BR06' mushrooms for other traits (Table 2), and corresponding measurements were taken from 17 trays of strain 'B14528' mushrooms (Table 3).

Table 2 below provides initial quantitative comparisons between mushroom strain 'RO14176' and strain 'BR06'. Column 1 lists the tray-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate $p<0.05$.

TABLE 2

| Characteristic | 'RO14176' Average | 'RO14176' St. Dev. | 'BR06' Average | 'BR06' St. Dev. | p-value |
|---|---|---|---|---|---|
| Before First Break | | | | | |
| Days to Pinset | 11.23 | 0.82 | 12.68 | 1.42 | **8.25E−05** |
| First Break | | | | | |
| Days to 1st Break | 17.46 | 1.03 | 18.53 | 1.71 | **1.27E−02** |
| Tray Coverage | 3.88 | 0.91 | 3.16 | 1.30 | **3.27E−02** |
| Cap Color Darkness | 3.85 | 0.37 | 4.21 | 0.42 | **3.46E−03** |
| Cap Firmness | 3.69 | 0.47 | 4.68 | 0.48 | **1.57E−08** |
| Cap Roundness (Visual) | 3.38 | 0.50 | 2.95 | 0.23 | **9.07E−04** |
| Yield (lb/ft$^2$) | 2.47 | 0.80 | 2.16 | 1.36 | 2.00E−01 |
| Second Break | | | | | |
| Days to 2nd Break | 24.42 | 0.86 | 24.95 | 0.91 | 5.48E−02 |
| Tray Coverage | 3.81 | 0.49 | 3.42 | 1.22 | 1.49E−01 |
| Cap Color Darkness | 3.58 | 0.50 | 4.05 | 0.23 | **4.15E−04** |
| Cap Firmness | 3.81 | 0.40 | 4.44 | 0.51 | **3.61E−05** |
| Cap Roundness (Visual) | 2.69 | 0.47 | 2.94 | 0.24 | **4.24E−02** |
| Yield (lb/ft$^2$) | 1.93 | 0.42 | 1.47 | 0.63 | **1.68E−04** |
| Third Break | | | | | |
| Yield (lb/ft$^2$) | 1.00 | 0.33 | 0.87 | 0.47 | 1.66E−01 |
| All Breaks Combined | | | | | |
| Yield (lb/ft$^2$) | 5.39 | 0.92 | 4.51 | 1.44 | **9.79E−04** |

Table 3 below provides initial quantitative comparisons between mushroom strain 'RO14176' and strain 'B14528'. Column 1 lists the tray-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate $p<0.05$.

TABLE 3

| Characteristic | 'RO14176' Average | 'RO14176' St. Dev. | 'B14528' Average | 'B14528' St. Dev. | p-value |
|---|---|---|---|---|---|
| Before First Break | | | | | |
| Days to Pinset | 11.23 | 0.82 | 11.41 | 0.87 | 4.92E−01 |
| First Break | | | | | |
| Days to 1st Break | 17.46 | 1.03 | 17.47 | 0.51 | 9.73E−01 |
| Tray Coverage | 3.88 | 0.91 | 3.59 | 0.87 | 2.94E−01 |
| Cap Color Darkness | 3.85 | 0.37 | 3.82 | 0.39 | 8.49E−01 |
| Cap Firmness | 3.69 | 0.47 | 3.88 | 0.33 | 1.56E−01 |
| Cap Roundness (Visual) | 3.38 | 0.50 | 2.88 | 0.33 | **7.05E−04** |
| Yield (lb/ft$^2$) | 2.47 | 0.80 | 2.39 | 0.54 | 7.11E−01 |
| Second Break | | | | | |
| Days to 2nd Break | 24.42 | 0.86 | 25.12 | 0.86 | **1.30E−02** |

TABLE 3-continued

| Characteristic | 'RO14176' Average | 'RO14176' St. Dev. | 'B14528' Average | 'B14528' St. Dev. | p-value |
|---|---|---|---|---|---|
| Tray Coverage | 3.81 | 0.49 | 3.47 | 0.51 | **3.67E−02** |
| Cap Color Darkness | 3.58 | 0.50 | 3.76 | 0.56 | 2.60E−01 |
| Cap Firmness | 3.81 | 0.40 | 3.82 | 0.39 | 8.99E−01 |
| Cap Roundness (Visual) | 2.69 | 0.47 | 2.82 | 0.39 | 3.47E−01 |
| Yield (lb/ft$^2$) | 1.93 | 0.42 | 1.74 | 0.38 | 1.09E−01 |
| Third Break | | | | | |
| Yield (lb/ft$^2$) | 1.00 | 0.33 | 1.18 | 0.38 | 6.16E−02 |
| All Breaks Combined | | | | | |
| Yield (lb/ft$^2$) | 5.39 | 0.92 | 5.31 | 0.76 | 7.45E−01 |

Individual Mushroom-Level Comparisons

In additional evidence of the distinctness and superiority of mushroom strain 'RO14176', provided below is a summary of precise quantitative measurements of individual mushrooms at first and second breaks. These data compare Cap L* Value, Cap a* Value, and Cap b* Values in the CIELAB color space, Cap Diameter, Cap Height, Cap Flesh Thickness, Stipe Diameter, Relative Cap Height, Relative Cap Flesh Thickness, and Relative Stipe Diameter (as described in Table 1). Measurements from 210 first break and 130 second break 'RO14176' mushrooms were compared to 350 first break and 130 second break 'BR06' mushrooms (Table 4) and 90 first break and 40 second break 'B14528' mushrooms (Table 5).

Table 4 below provides initial quantitative comparisons between mushroom strain 'RO14176' and strain 'BR06'. Column 1 lists the mushroom-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'BR06', column 5 shows the standard deviation of the characteristic for mushroom strain 'BR06', and column 6 shows the p-values of two-sample, two-sided t-tests. Bolded p-values indicate $p<0.05$.

TABLE 4

| Characteristic | 'RO14176' Average | 'RO14176' St. Dev. | 'BR06' Average | 'BR06' St. Dev. | p-value |
|---|---|---|---|---|---|
| First Break | | | | | |
| Cap L* Value (dark-light) | 65.73 | 4.23 | 63.49 | 6.52 | **1.00E−05** |
| Cap a* Value (green-red) | 7.64 | 1.00 | 8.53 | 1.85 | **2.45E−10** |
| Cap b* Value (blue-yellow) | 26.84 | 1.43 | 28.15 | 2.48 | **7.83E−12** |
| Cap Diameter | 43.93 | 3.61 | 42.78 | 4.41 | **1.45E−03** |
| Cap Height | 28.15 | 2.18 | 25.75 | 2.35 | **1.27E−29** |
| Cap Flesh Thickness | 15.37 | 1.96 | 13.25 | 1.46 | **1.88E−44** |
| Stipe Diameter | 19.92 | 2.43 | 19.25 | 2.47 | **1.19E−03** |
| Relative Cap Height | 0.64 | 0.03 | 0.60 | 0.04 | **4.25E−33** |
| Relative Cap Flesh Thickness | 0.35 | 0.04 | 0.31 | 0.03 | **3.34E−39** |
| Relative Stipe Diameter | 0.45 | 0.05 | 0.45 | 0.06 | 5.18E−01 |
| Second Break | | | | | |
| Cap L* Value (dark-light) | 68.87 | 3.95 | 64.27 | 3.81 | **5.37E−20** |
| Cap a* Value (green-red) | 6.66 | 0.95 | 8.20 | 1.14 | **1.67E−27** |
| Cap b* Value (blue-yellow) | 26.77 | 1.64 | 28.31 | 1.65 | **1.08E−13** |
| Cap Diameter | 42.13 | 3.35 | 43.26 | 4.15 | **1.32E−02** |
| Cap Height | 26.36 | 2.27 | 25.80 | 2.61 | 5.55E−02 |
| Cap Flesh Thickness | 14.15 | 1.77 | 13.46 | 1.52 | **6.12E−04** |
| Stipe Diameter | 17.80 | 2.58 | 18.97 | 3.67 | **2.54E−03** |
| Relative Cap Height | 0.63 | 0.05 | 0.60 | 0.04 | **1.01E−07** |
| Relative Cap Flesh Thickness | 0.34 | 0.04 | 0.31 | 0.03 | **1.18E−07** |
| Relative Stipe Diameter | 0.42 | 0.05 | 0.44 | 0.08 | **3.93E−02** |

Table 5 below provides initial quantitative comparisons between mushroom strain 'RO14176' and strain 'B14528'. Column 1 lists the mushroom-level characteristics (as described in Table 1), column 2 shows the average value of the characteristic for mushroom strain 'RO14176', column 3 shows the standard deviation of the characteristic for mushroom strain 'RO14176', column 4 shows the average value of the characteristic for mushroom strain 'B14528', column 5 shows the standard deviation of the characteristic for mushroom strain 'B14528', and column 6 shows the p-values of two-sample, two-sided t-tests. Bolded p-values indicate $p<0.05$.

TABLE 5

| Characteristic | 'RO14176' Average | 'RO14176' St. Dev. | 'B14528' Average | 'B14528' St. Dev. | p-value |
|---|---|---|---|---|---|
| First Break | | | | | |
| Cap L* Value (dark-light) | 65.73 | 4.23 | 64.48 | 5.25 | **2.98E−02** |
| Cap a* Value (green-red) | 7.64 | 1.00 | 8.03 | 1.65 | **1.30E−02** |
| Cap b* Value (blue-yellow) | 26.84 | 1.43 | 29.38 | 1.50 | **3.68E−34** |
| Cap Diameter | 43.93 | 3.61 | 43.84 | 3.80 | 8.49E−01 |
| Cap Height | 28.15 | 2.18 | 26.60 | 1.97 | **1.91E−08** |
| Cap Flesh Thickness | 15.37 | 1.96 | 12.91 | 0.93 | **2.05E−27** |
| Stipe Diameter | 19.92 | 2.43 | 17.58 | 1.44 | **3.66E−17** |
| Relative Cap Height | 0.64 | 0.03 | 0.61 | 0.03 | **1.59E−15** |
| Relative Cap Flesh Thickness | 0.35 | 0.04 | 0.30 | 0.03 | **2.71E−28** |
| Relative Stipe Diameter | 0.45 | 0.05 | 0.40 | 0.04 | **2.36E−18** |

TABLE 5-continued

| Characteristic | 'RO14176' Average | 'RO14176' St. Dev. | 'B14528' Average | 'B14528' St. Dev. | p-value |
|---|---|---|---|---|---|
| Second Break | | | | | |
| Cap L* Value (dark-light) | 68.87 | 3.95 | 68.52 | 4.46 | 6.36E-01 |
| Cap a* Value (green-red) | 6.66 | 0.95 | 7.88 | 1.49 | **7.36E-09** |
| Cap b* Value (blue-yellow) | 26.77 | 1.64 | 28.55 | 1.65 | **1.30E-08** |
| Cap Diameter | 42.13 | 3.35 | 44.86 | 3.59 | **1.67E-05** |
| Cap Height | 26.36 | 2.27 | 26.29 | 1.72 | 8.51E-01 |
| Cap Flesh Thickness | 14.15 | 1.77 | 12.60 | 1.32 | **8.12E-07** |
| Stipe Diameter | 17.80 | 2.58 | 18.11 | 3.29 | 5.33E-01 |
| Relative Cap Height | 0.63 | 0.05 | 0.59 | 0.04 | **1.36E-05** |
| Relative Cap Flesh Thickness | 0.34 | 0.04 | 0.28 | 0.03 | **9.66E-13** |
| Relative Stipe Diameter | 0.42 | 0.05 | 0.40 | 0.07 | 9.03E-02 |

Additional Trials

Tray-Level Comparisons

Several additional trials were conducted for characterizing 'RO14176'. In further evidence of the distinctness and superiority of mushroom strain 'RO14176', provided below are the results of trials conducted across multiple strains' yielded trays of mushrooms. These trials compare timing for trays to reach pinset and harvestable maturity, and yield at each break.

Table 6 below provides further quantitative comparisons between mushroom strain 'RO14176' and strain 'BR06'.

The first part of analyzing trait measurements in the additional trials herein included making comparisons between all three of instant strain 'RO14176', comparative strain 'BR06', and comparative strain 'B14528'. For these three strains, a Shapiro-Wilk test and a Levene test were performed first to assess if the data satisfy the assumptions of normality and equal variances among groups, respectively, of a standard ANOVA. The Shapiro-Wilk test and Levene test determined that most of these traits satisfied neither assumption. Therefore, a Kruskal-Wallis test (Kruskal, W. H., & Wallis, W. A. (1952). Use of ranks in one-criterion variance analysis. Journal of the American statistical Association, 47(260), 583-621), a non-parametric variation of ANOVA that does not assume normality, equal variances among groups, or equal sample sizes among groups, was performed. Medians and interquartile ranges (IQR) were reported, as these metrics are robust to non-normal distributions. Means are also reported for consistency with normally-distributed traits.

The Shapiro-Wilk test and Levene test determined that most developmental timing traits (Days to Pinset, Days to 1st Break, and Days to 2nd Break) and yield traits were not normally distributed and variances among groups were not equal. The Kruskal-Wallis test and Dunn post-hoc test ("Dunn's Test"; Dunn, O. J. (1964). Multiple comparisons using rank sums. Technometrics, 6(3), 241-252) were used in these cases. When the Kruskal-Wallis test results were significant based on a threshold of $p<0.05$, Dunn's test was performed post-hoc to make pairwise strain comparisons (Dunn, 1964). P-values were adjusted using the Bonferroni correction to minimize risk of Type 1 error (false significance). An exception to this trend was Percent Harvested Speed, which was normally distributed and exhibited equal variance for all strains. For assessing Percent Harvested Speed, a standard ANOVA was used and a Tukey Honestly Significant Difference (HSD) test was performed post-hoc for pairwise strain comparisons. Standard deviations multiplied by 100 for consistency alongside percentages ("SD*100") were reported for this trait. This testing was performed on groups of three strains, but the results show a pairwise subset of the tests for consistency with the initial trials.

In Table 6, column 1 shows each trait and the strains compared for said trait, column 2 shows the mean value for that strain's measurements of that trait, column 3 shows the median value of the same measurements, column 4 shows the interquartile range (IQR) for the same measurements, column 5 shows the number of trials conducted, and column 6 shows the statistical significance group calculated for that strain for that trait according to Dunn's Test. Traits of particular interest are bolded.

TABLE 6

| Variety | Mean | Median | IQR | Number of Trials | Significance Group (Dunn's Test) |
|---|---|---|---|---|---|
| Before First Break Days to Pinset | | | | | |
| 'RO14176' | 11.4 | 12.0 | 1.00 | 7 | a |
| 'BR06' | 12.7 | 12.5 | 1.00 | 7 | b |
| First Break Days to 1st Break | | | | | |
| 'RO14176' | 17.7 | 18.0 | 1.00 | 7 | a |
| 'BR06' | 18.8 | 18.0 | 2.00 | 7 | b |
| Yield (kg/m$^2$) | | | | | |
| 'RO14176' | 12.40 | 12.25 | 4.69 | 6 | a |
| 'BR06' | 10.99 | 11.03 | 8.10 | 6 | a |
| Second Break Days to 2nd Break | | | | | |
| 'RO14176' | 25.3 | 25.0 | 2.00 | 7 | a |
| 'BR06' | 25.9 | 26.0 | 2.00 | 7 | b |
| Yield (kg/m$^2$) | | | | | |
| 'RO14176' | 8.45 | 8.50 | 3.52 | 6 | a |
| 'BR06' | 7.37 | 6.59 | 5.13 | 6 | a |
| Third Break Yield (kg/m$^2$) | | | | | |
| 'RO14176' | 4.20 | 3.71 | 2.69 | 6 | a |
| 'BR06' | 3.27 | 2.34 | 3.03 | 6 | b |
| All Breaks Combined Yield (kg/m$^2$) | | | | | |
| 'RO14176' | 25.05 | 23.88 | 3.66 | 6 | a |
| 'BR06' | 21.58 | 22.02 | 4.39 | 6 | b |
| Percent Harvested Speed (measured in First Break) | | | SD * 100 | | Significance Group (Tukey HSD) |
| 'RO14176' | 38.7% | 39.9% | 13.10 | 5 | b |
| 'BR06' | 14.5% | 12.9% | 16.90 | 5 | a |

Table 7 below provides additional quantitative comparison between mushroom strain 'RO14176' and strain 'B14528'. Column 1 shows the strains compared for each trait, column 2 shows the mean value for that strain's measurements, column 3 shows the median value of the same measurements, column 4 shows either the interquartile range (IQR) or the standard deviation multiplied by 100 for consistency alongside percentages ("SD*100") for the same measurements, column 5 shows the number of trials conducted, and column 6 shows the statistical significance group calculated for that strain for that trait according to either Dunn's Test or Tukey HSD.

TABLE 7

| Characteristic | Mean | Median | IQR | Number of Trials | Significance Group (Dunn's Test) |
|---|---|---|---|---|---|
| Before First Break Days to Pinset | | | | | |
| 'RO14176' | 11.4 | 12.0 | 1.00 | 7 | a |
| 'B14528' | 11.2 | 11.0 | 1.50 | 7 | a |
| First Break Days to 1st Break | | | | | |
| 'RO14176' | 17.7 | 18.0 | 1.00 | 7 | a |
| 'B14528' | 17.6 | 18.0 | 1.00 | 7 | a |
| Yield (kg/m$^2$) | | | | | |
| 'RO14176' | 12.40 | 12.25 | 4.69 | 6 | a |
| 'B14528' | 11.91 | 12.21 | 4.35 | 6 | a |
| Second Break Days to 2nd Break | | | | | |
| 'RO14176' | 25.3 | 25.0 | 2.00 | 7 | a |
| 'B14528' | 25.5 | 25.0 | 1.00 | 7 | ab |
| Yield (kg/m$^2$) | | | | | |
| 'RO14176' | 8.45 | 8.50 | 3.52 | 6 | a |
| 'B14528' | 7.47 | 7.76 | 2.93 | 6 | a |
| Third Break Yield (kg/m$^2$) | | | | | |
| 'RO14176' | 4.20 | 3.71 | 2.69 | 6 | a |
| 'B14528' | 4.49 | 3.95 | 2.59 | 6 | a |
| All Breaks Combined Yield (kg/m$^2$) | | | | | |
| 'RO14176' | 25.05 | 23.88 | 3.66 | 6 | a |
| 'B14528' | 23.88 | 23.97 | 6.69 | 6 | a |
| Percent Harvested Speed (measured in First Break) | Mean | Median | SD * 100 | | Significance Group (Tukey HSD) |
| 'RO14176' | 38.7% | 39.9% | 13.10 | 5 | b |
| 'B14528' | 41.8% | 40.3% | 7.60 | 5 | b |

Table 8 below provides additional quantitative comparison between mushroom strain 'RO14176' and strain 'RO10425'. Column 1 shows the strains compared for each trait, column 2 shows the mean value for that strain's measurements, column 3 shows the median value of the same measurements, column 4 shows either the interquartile range (IQR) or the standard deviation multiplied by 100 for consistency alongside percentages ("SD*100") for the same measurements, column 5 shows the number of trials conducted, and column 6 shows the statistical significance group calculated for that strain for that trait according to either Dunn's Test or Tukey HSD.

TABLE 8

| Characteristic | Mean | Median | IQR | Number of Trials | Significance Group (Dunn's Test) |
|---|---|---|---|---|---|
| Before First Break Days to Pinset | | | | | |
| 'RO10425' | 12.00 | 12.00 | 2.00 | 4 | a |
| 'RO14176' | 11.44 | 12.00 | 1.00 | 7 | a |
| First Break Days to 1st Break | | | | | |
| 'RO10425' | 18.00 | 18.00 | 1.00 | 4 | a |
| 'RO14176' | 17.71 | 18.00 | 1.00 | 7 | a |
| Yield (kg/m$^2$) | | | | | |
| 'RO10425' | 10.64 | 10.64 | 1.76 | 3 | a |
| 'RO14176' | 12.40 | 12.25 | 4.69 | 6 | a |
| Second Break Days to 2nd Break | | | | | |
| 'RO10425' | 24.86 | 25.00 | 1.75 | 4 | a |
| 'RO14176' | 25.28 | 25.00 | 2.00 | 7 | a |
| Yield (kg/m$^2$) | | | | | |
| 'RO10425' | 8.74 | 8.10 | 3.27 | 3 | a |
| 'RO14176' | 8.45 | 8.50 | 3.52 | 6 | a |
| Third Break Yield (kg/m$^2$) | | | | | |
| 'RO10425' | 3.66 | 3.52 | 0.78 | 3 | a |
| 'RO14176' | 4.20 | 3.71 | 2.69 | 6 | a |
| All Breaks Combined Yield (kg/m$^2$) | | | | | |
| 'RO10425' | 23.05 | 23.14 | 4.25 | 3 | a |
| 'RO14176' | 25.05 | 23.88 | 3.66 | 6 | a |
| Percent Harvested Speed (measured in First Break) | Mean | Median | SD * 100 | | Significance Group (Tukey HSD) |
| 'RO10425' | 36.7% | 34.8% | 32.7% | 3 | a |
| 'RO14176' | 38.7% | 39.9% | 13.1% | 5 | a |

Table 9 below provides additional quantitative comparison between mushroom strain 'RO14176' and strain 'RO12756' (U.S. application Ser. No. 19/305,683). Column 1 shows the strains compared for each trait, column 2 shows the mean value for that strain's measurements, column 3 shows the median value of the same measurements, column 4 shows either the interquartile range (IQR) or the standard deviation multiplied by 100 for consistency alongside percentages ("SD*100") for the same measurements, column 5 shows the number of trials conducted, and column 6 shows the statistical significance group calculated for that strain for that trait according to either Dunn's Test or Tukey HSD.

TABLE 9

| Characteristic | Mean | Median | IQR | Number of Trials | Significance Group (Dunn's Test) |
|---|---|---|---|---|---|
| Before First Break Days to Pinset | | | | | |
| 'RO12756' | 11.42 | 11.00 | 1.00 | 8 | a |
| 'RO14176' | 11.44 | 12.00 | 1.00 | 7 | a |

TABLE 9-continued

| | | | | | |
|---|---|---|---|---|---|
| | | First Break<br>Days to 1st Break | | | |
| 'RO12756' | 17.51 | 17.00 | 1.00 | 8 | a |
| 'RO14176' | 17.71 | 18.00 | 1.00 | 7 | a |
| | | Yield (kg/m$^2$) | | | |
| 'RO12756' | 11.91 | 12.40 | 4.88 | 8 | a |
| 'RO14176' | 12.40 | 12.25 | 4.69 | 6 | a |
| | | Second Break<br>Days to 2nd Break | | | |
| 'RO12756' | 24.84 | 25.00 | 2.00 | 7 | a |
| 'RO14176' | 25.28 | 25.00 | 2.00 | 7 | a |
| | | Yield (kg/m$^2$) | | | |
| 'RO12756' | 8.54 | 8.15 | 2.64 | 8 | a |
| 'RO14176' | 8.45 | 8.50 | 3.52 | 6 | a |
| | | Third Break<br>Yield (kg/m$^2$) | | | |
| 'RO12756' | 4.78 | 4.83 | 1.86 | 8 | a |
| 'RO14176' | 4.20 | 3.71 | 2.69 | 6 | a |
| | | All Breaks Combined<br>Yield (kg/m$^2$) | | | |
| 'RO12756' | 25.29 | 24.95 | 4.15 | 8 | a |
| 'RO14176' | 25.05 | 23.88 | 3.66 | 6 | a |

| Percent Harvested Speed (measured in First Break) | Mean | Median | SD * 100 | | Significance Group (Tukey HSD) |
|---|---|---|---|---|---|
| 'RO12756' | 48.2% | 50.9% | 16.3% | 8 | a |
| 'RO14176' | 38.7% | 39.9% | 13.1% | 5 | a |

Individual Mushroom-Level Comparisons

In additional evidence of the distinctness and superiority of mushroom strain 'RO14176', provided below is a summary of precise quantitative measurements of individual mushrooms at first and second breaks. These data compare Cap L* Value, Cap a* Value, and Cap b* Values in the CIELAB color space, Cap Apex Flesh Thickness, Cap Edge Flesh Thickness, and Cap Roundness (Calculated) (as described in Table 1). Measurements were taken for hundreds of mushrooms per trait, noted as sample size (n) in Tables 10 and 11B.

Table 10 below provides additional quantitative comparisons between mushroom strain 'RO14176' and strain 'BR06'. Column 1 shows each trait and the strains compared for said trait, column 2 shows the mean value for that strain's measurements of that trait, column 3 shows the median value of the same measurements, column 4 shows the interquartile range (IQR) for the same measurements, column 5 shows the number of mushrooms assessed (n), and column 6 shows the statistical significance group calculated for that strain for that trait according to Dunn's Test.

TABLE 10

| Variety | Mean | Median | IQR | Number of Mushrooms (n) | Significance Group (Dunn's Test) |
|---|---|---|---|---|---|
| | | First Break<br>Cap L* Value (dark-light) | | | |
| 'RO14176' | 65.76 | 65.82 | 5.82 | 469 | a |
| 'BR06' | 63.30 | 62.74 | 9.83 | 797 | b |

TABLE 10-continued

| Variety | Mean | Median | IQR | Number of Mushrooms (n) | Significance Group (Dunn's Test) |
|---|---|---|---|---|---|
| | | Cap a* Value (green-red) | | | |
| 'RO14176' | 7.45 | 7.47 | 1.58 | 469 | a |
| 'BR06' | 8.67 | 8.96 | 2.58 | 787 | b |
| | | Cap b* Value (blue-yellow) | | | |
| 'RO14176' | 28.17 | 28.03 | 2.64 | 469 | a |
| 'BR06' | 28.72 | 29.04 | 3.17 | 776 | b |
| | | Cap Apex Flesh Thickness | | | |
| 'RO14176' | 0.54 | 0.54 | 0.06 | 453 | a |
| 'BR06' | 0.52 | 0.52 | 0.05 | 541 | b |
| | | Cap Edge Flesh Thickness | | | |
| 'RO14176' | 0.27 | 0.26 | 0.07 | 449 | a |
| 'BR06' | 0.21 | 0.21 | 0.09 | 537 | b |
| | | Cap Roundness (Calculated) | | | |
| 'RO14176' | 0.64 | 0.64 | 0.05 | 455 | a |
| 'BR06' | 0.61 | 0.61 | 0.04 | 541 | b |
| | | Second Break<br>Cap L* Value (dark-light) | | | |
| 'RO14176' | 68.92 | 68.86 | 6.39 | 263 | a |
| 'BR06' | 65.68 | 65.49 | 5.90 | 340 | b |
| | | Cap a* Value (green-red) | | | |
| 'RO14176' | 6.37 | 6.43 | 1.60 | 261 | a |
| 'BR06' | 7.21 | 7.31 | 2.42 | 340 | b |
| | | Cap b* Value (blue-yellow) | | | |
| 'RO14176' | 27.36 | 27.35 | 2.11 | 261 | a |
| 'BR06' | 28.15 | 28.49 | 2.86 | 340 | b |
| | | Cap Apex Flesh Thickness | | | |
| 'RO14176' | 0.54 | 0.54 | 0.04 | 235 | a |
| 'BR06' | 0.51 | 0.52 | 0.07 | 362 | b |
| | | Cap Edge Flesh Thickness | | | |
| 'RO14176' | 0.31 | 0.31 | 0.06 | 235 | a |
| 'BR06' | 0.23 | 0.23 | 0.09 | 362 | b |
| | | Cap Roundness (Calculated) | | | |
| 'RO14176' | 0.61 | 0.60 | 0.05 | 235 | a |
| 'BR06' | 0.60 | 0.59 | 0.06 | 363 | b |

Table 11A below provides qualitative comparisons between mushroom strain 'RO14176' and strain 'B14528'. Column 1 lists the mushroom-level characteristics (as described in Table 1), column 2 shows the qualitative descriptor for the characteristic for mushroom strain 'RO14176' relative to 'B14528', and column 3 shows the qualitative descriptor for mushroom strain 'B14528' relative to 'RO14176'.

TABLE 11A

| Characteristic | 'RO14176' | 'B14528' |
|---|---|---|
| First Break | | |
| Cap L* Value (dark-light) | Lighter | Darker |
| Cap a* Value (green-red) | Greener | Redder |
| Cap b* Value (blue-yellow) | Bluer | Yellower |
| Cap Apex Flesh Thickness | Thicker | Thinner |
| Cap Edge Flesh Thickness | Thicker | Thinner |
| Cap Roundness (Calculated) | Rounder | Flatter |
| Second Break | | |
| Cap L* Value (dark-light) | Similar | Similar |
| Cap a* Value (green-red) | Redder | Greener |

TABLE 11A-continued

| Characteristic | 'RO14176' | 'B14528' |
|---|---|---|
| Cap b* Value (blue-yellow) | Similar | Similar |
| Cap Apex Flesh Thickness | Thicker | Thinner |
| Cap Edge Flesh Thickness | Thicker | Thinner |
| Cap Roundness (Calculated) | Rounder | Flatter |

Table 11B shows additional quantitative comparisons between mushroom strain 'RO14176' and strain 'B14528'. Column 1 shows each trait and the strains compared for said trait, column 2 shows the mean value for that strain's measurements of that trait, column 3 shows the median value of the characteristic, column 4 shows the interquartile range (IQR) for the characteristic, column 5 shows the number of mushrooms assessed (n), and column 6 shows the statistical significance group calculated according to Dunn's Test.

TABLE 11B

| Variety | Mean | Median | IQR | Number of Mushrooms (n) | Significance Group (Dunn's Test) |
|---|---|---|---|---|---|
| First Break | | | | | |
| Cap L* Value (dark-light) | | | | | |
| 'RO14176' | 65.76 | 65.82 | 5.82 | 469 | a |
| 'B14528' | 64.06 | 64.13 | 6.56 | 340 | c |
| Cap a* Value (green-red) | | | | | |
| 'RO14176' | 7.45 | 7.47 | 1.58 | 469 | a |
| 'B14528' | 8.26 | 8.31 | 2.13 | 340 | c |
| Cap b* Value (blue-yellow) | | | | | |
| 'RO14176' | 28.17 | 28.03 | 2.64 | 469 | a |
| 'B14528' | 30.31 | 30.16 | 3.39 | 340 | c |
| Cap Apex Flesh Thickness | | | | | |
| 'RO14176' | 0.54 | 0.54 | 0.06 | 453 | a |
| 'B14528' | 0.47 | 0.46 | 0.06 | 387 | c |
| Cap Edge Flesh Thickness | | | | | |
| 'RO14176' | 0.27 | 0.26 | 0.07 | 449 | a |
| 'B14528' | 0.22 | 0.22 | 0.08 | 387 | b |
| Cap Roundness (Calculated) | | | | | |
| 'RO14176' | 0.64 | 0.64 | 0.05 | 455 | a |
| 'B14528' | 0.61 | 0.61 | 0.05 | 389 | b |
| Second Break | | | | | |
| Cap L* Value (dark-light) | | | | | |
| 'RO14176' | 68.92 | 68.86 | 6.39 | 263 | a |
| 'B14528' | 68.56 | 69.02 | 6.54 | 170 | a |
| Cap a* Value (green-red) | | | | | |
| 'RO14176' | 6.37 | 6.43 | 1.60 | 261 | a |
| 'B14528' | 6.09 | 5.96 | 2.05 | 170 | c |
| Cap b* Value (blue-yellow) | | | | | |
| 'RO14176' | 27.36 | 27.35 | 2.11 | 261 | a |
| 'B14528' | 27.37 | 27.78 | 3.22 | 170 | a |
| Cap Apex Flesh Thickness | | | | | |
| 'RO14176' | 0.54 | 0.54 | 0.04 | 235 | a |
| 'B14528' | 0.46 | 0.46 | 0.05 | 198 | c |
| Cap Edge Flesh Thickness | | | | | |
| 'RO14176' | 0.31 | 0.31 | 0.06 | 235 | a |
| 'B14528' | 0.23 | 0.23 | 0.06 | 198 | b |
| Cap Roundness (Calculated) | | | | | |
| 'RO14176' | 0.61 | 0.60 | 0.05 | 235 | a |
| 'B14528' | 0.60 | 0.60 | 0.05 | 198 | b |

One of the advantages of the strain 'RO14176' is its incompatibility with other commercial strains. Table 12 below provides results of compatibility tests between strain 'RO14176' and commercial strain 'BR06', commercial strain 'B14528', or related strain 'RO10425'. These results indicate that strain 'RO14176' is incompatible with strain 'BR6' and strain 'B14528', and compatible with related strain 'RO10425'. This was true regardless of which tested strain served as the compost variety and which tested strain served as the casing variety.

TABLE 12

| Strains (compost variety/ casing variety) | Mean | | Median | |
|---|---|---|---|---|
| | lb/ft$^2$ | kg/m$^2$ | lb/ft$^2$ | kg/m$^2$ |
| 'RO14176'/ 'RO14176' | 2.66 | 12.99 | 2.41 | 11.77 |
| 'RO10425'/ 'RO10425' | 2.71 | 13.23 | 2.86 | 13.94 |
| 'BR06'/ 'BR06' | 2.62 | 12.79 | 2.46 | 11.99 |
| 'B14528'/ 'B14528' | 2.93 | 14.31 | 2.92 | 14.23 |
| 'RO10425'/ 'RO14176', 'RO14176'/ 'RO10425' | 2.43 | 11.86 | 2.75 | 13.40 |
| 'RO14176'/ 'BR06', 'BR06'/ 'RO14176' | 1.19 | 5.81 | 1.20 | 5.86 |
| 'RO14176'/ 'B14528', 'B14528'/ 'RO14176' | 0.70 | 3.42 | 0.76 | 3.69 |

| Strains (compost variety/ casing variety) | SD | | Trials | Significance Group |
|---|---|---|---|---|
| | lb/ft$^2$ | kg/m$^2$ | | |
| 'RO14176'/ 'RO14176' | 0.61 | 2.98 | 3 | a |
| 'RO10425'/ 'RO10425' | 0.50 | 2.44 | 3 | a |
| 'BR06'/ 'BR06' | 1.15 | 5.61 | 2 | a |
| 'B14528'/ 'B14528' | 0.34 | 1.66 | 1 | a |
| 'RO10425'/ 'RO14176', 'RO14176'/ 'RO10425' | 0.77 | 3.76 | 1 | a |
| 'RO14176'/ 'BR06', 'BR06'/ 'RO14176' | 0.37 | 1.81 | 1 | b |
| 'RO14176'/ 'B14528', 'B14528'/ 'RO14176' | 0.21 | 1.03 | 1 | b |

Table 13 below shows quantitative comparisons between mushroom strain 'RO14176' and strain 'RO14175'. Column 1 shows each trait and the strains compared for said trait, column 2 shows the mean value for that strain's measurements of that trait, column 3 shows the median value of the characteristic, column 4 shows the interquartile range (IQR) for the characteristic, column 5 shows the number of mushrooms assessed (n), and column 6 shows the statistical significance group calculated according to Dunn's Test.

TABLE 13

| Variety | Mean | Median | IQR | Number of Mushrooms (n) | Significance Group (Dunn's Test) |
|---|---|---|---|---|---|
| First Break Cap L* Value (dark-light) | | | | | |
| 'RO10425' | 65.66 | 65.22 | 7.34 | 209 | a |
| 'RO14176' | 65.76 | 65.82 | 5.82 | 469 | a |
| Cap a* Value (green-red) | | | | | |
| 'RO10425' | 7.35 | 7.43 | 1.97 | 209 | a |
| 'RO14176' | 7.45 | 7.47 | 1.58 | 469 | a |
| Cap b* Value (blue-yellow) | | | | | |
| 'RO10425' | 28.43 | 28.58 | 3.10 | 209 | a |
| 'RO14176' | 28.17 | 28.03 | 2.64 | 469 | a |
| Cap Apex Flesh Thickness | | | | | |
| 'RO10425' | 0.55 | 0.55 | 0.04 | 166 | a |
| 'RO14176' | 0.54 | 0.54 | 0.06 | 453 | b |
| Cap Edge Flesh Thickness | | | | | |
| 'RO10425' | 0.30 | 0.31 | 0.05 | 166 | a |
| 'RO14176' | 0.27 | 0.26 | 0.07 | 449 | c |
| Cap Roundness (Calculated) | | | | | |
| 'RO10425' | 0.64 | 0.63 | 0.05 | 166 | a |
| 'RO14176' | 0.64 | 0.64 | 0.05 | 455 | c |
| Second Break Cap L* Value (dark-light) | | | | | |
| 'RO10425' | 68.82 | 69.47 | 8.2 | 157 | a |
| 'RO14176' | 68.92 | 68.86 | 6.39 | 263 | a |
| Cap a* Value (green-red) | | | | | |
| 'RO10425' | 6.15 | 6.26 | 2.55 | 157 | a |
| 'RO14176' | 6.37 | 6.43 | 1.60 | 261 | a |
| Cap b* Value (blue-yellow) | | | | | |
| 'RO10425' | 27.69 | 27.46 | 2.54 | 157 | a |
| 'RO14176' | 27.36 | 27.35 | 2.11 | 261 | a |
| Cap Apex Flesh Thickness | | | | | |
| 'RO10425' | 0.55 | 0.55 | 0.04 | 157 | a |
| 'RO14176' | 0.54 | 0.54 | 0.04 | 235 | a |
| Cap Edge Flesh Thickness | | | | | |
| 'RO10425' | 0.32 | 0.32 | 0.05 | 157 | a |
| 'RO14176' | 0.31 | 0.31 | 0.06 | 235 | c |
| Cap Roundness (Calculated) | | | | | |
| 'RO10425' | 0.61 | 0.61 | 0.05 | 157 | a |
| 'RO14176' | 0.61 | 0.60 | 0.05 | 235 | a |

Table 14 below shows quantitative comparisons between mushroom strain 'RO14176' and strain 'RO12756'. Column 1 shows each trait and the strains compared for said trait, column 2 shows the mean value for that strain's measurements of that trait, column 3 shows the median value of the characteristic, column 4 shows the interquartile range (IQR) for the characteristic, column 5 shows the number of mushrooms assessed (n), and column 6 shows the statistical significance group calculated according to Dunn's Test.

TABLE 14

| Variety | Mean | Median | IQR | Number of Mushrooms (n) | Significance Group (Dunn's Test) |
|---|---|---|---|---|---|
| First Break Cap L* Value (dark-light) | | | | | |
| 'RO12756' | 72.12 | 72.29 | 4.81 | 580 | b |
| 'RO14176' | 65.76 | 65.82 | 5.82 | 469 | a |
| Cap a* Value (green-red) | | | | | |
| 'RO12756' | 5.62 | 5.66 | 1.88 | 580 | b |
| 'RO14176' | 7.45 | 7.47 | 1.58 | 469 | a |
| Cap b* Value (blue-yellow) | | | | | |
| 'RO12756' | 26.98 | 27.06 | 4.11 | 580 | b |
| 'RO14176' | 28.17 | 28.03 | 2.64 | 469 | a |
| Cap Apex Flesh Thickness | | | | | |
| 'RO12756' | 0.55 | 0.55 | 0.06 | 575 | a |
| 'RO14176' | 0.54 | 0.54 | 0.06 | 453 | b |
| Cap Edge Flesh Thickness | | | | | |
| 'RO12756' | 0.22 | 0.23 | 0.10 | 569 | b |
| 'RO14176' | 0.27 | 0.26 | 0.07 | 449 | c |
| Cap Roundness (Calculated) | | | | | |
| 'RO12756' | 0.61 | 0.61 | 0.04 | 579 | b |
| 'RO14176' | 0.64 | 0.64 | 0.05 | 455 | c |
| Second Break Cap L* Value (dark-light) | | | | | |
| 'RO12756' | 73.02 | 72.87 | 4.35 | 200 | b |
| 'RO14176' | 68.92 | 68.86 | 6.39 | 263 | a |
| Cap a* Value (green-red) | | | | | |
| 'RO12756' | 4.84 | 4.95 | 1.64 | 200 | b |
| 'RO14176' | 6.37 | 6.43 | 1.60 | 261 | a |
| Cap b* Value (blue-yellow) | | | | | |
| 'RO12756' | 26.55 | 26.83 | 3.24 | 200 | b |
| 'RO14176' | 27.36 | 27.35 | 2.11 | 261 | a |
| Cap Apex Flesh Thickness | | | | | |
| 'RO12756' | 0.54 | 0.54 | 0.04 | 198 | a |
| 'RO14176' | 0.54 | 0.54 | 0.04 | 235 | a |
| Cap Edge Flesh Thickness | | | | | |
| 'RO12756' | 0.27 | 0.27 | 0.10 | 199 | b |
| 'RO14176' | 0.31 | 0.31 | 0.06 | 235 | c |
| Cap Roundness (Calculated) | | | | | |
| 'RO12756' | 0.56 | 0.56 | 0.05 | 199 | b |
| 'RO14176' | 0.61 | 0.60 | 0.05 | 235 | a |

What is claimed is:

1. A new and distinct variety of *Agaricus bisporus* Imbach mushroom named 'RO14176', as shown and described herein.

* * * * *